(12) United States Patent
Johnson

(10) Patent No.: US 7,524,286 B2
(45) Date of Patent: *Apr. 28, 2009

(54) SYSTEM FOR COMBINED TRANSCUTANEOUS BLOOD GAS MONITORING AND NEGATIVE PRESSURE WOUND TREATMENT

(75) Inventor: Royce Johnson, Universal City, TX (US)

(73) Assignee: KCI Licensing, Inc., San Antonio, TX (US)

( * ) Notice: Subject to any disclaimer, the term of this patent is extended or adjusted under 35 U.S.C. 154(b) by 959 days.

This patent is subject to a terminal disclaimer.

(21) Appl. No.: 10/867,990

(22) Filed: Jun. 15, 2004

(65) Prior Publication Data

US 2004/0225208 A1     Nov. 11, 2004

Related U.S. Application Data

(63) Continuation of application No. 10/085,321, filed on Feb. 28, 2002, now Pat. No. 6,856,821, which is a continuation-in-part of application No. 09/579,755, filed on May 26, 2000, now abandoned.

(60) Provisional application No. 60/136,293, filed on May 27, 1999.

(51) Int. Cl.
*A61B 5/00*     (2006.01)
(52) U.S. Cl. .................. 600/309; 600/345; 600/304
(58) Field of Classification Search .................. None
See application file for complete search history.

(56) References Cited

U.S. PATENT DOCUMENTS 1,355,846  A     10/1920  Rannells (Continued)

FOREIGN PATENT DOCUMENTS

AU         550575  A1     8/1982

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery, . . . .

(Continued)

*Primary Examiner*—Robert L. Nasser, Jr.

(57) ABSTRACT

A method and apparatus for the transcutaneous monitoring of blood gases generally comprises a blood gas data acquisition device, a vacuum source and a blood gas transducer unit. The blood gas transducer unit is adapted for application to a patient's skin and administration of a local vacuum at the area of patient application. It further comprises an electrochemical blood gas transducer, well known to those of ordinary skill in the art, which is disposed entirely within the local vacuum at the area of patient application. The vacuum source is placed in fluid communication with the blood gas transducer unit, through a hydrophobic membrane filter for safety purposes, in order to induce a condition of hyperperfusion in the locality of the electrochemical blood gas transducer. Under the control of a microcontroller, or equivalent means, the blood gas acquisition device is then utilized to capture a measure of skin surface oxygen or carbon dioxide pressure. The microcontroller can then utilize this measure to arrive at an estimate of arterial partial pressure of oxygen or carbon dioxide, accordingly. Because vacuum induced perfusion produces the requisite condition of hyperperfusion without local heating and, therefore, without acceleration of the local metabolic function, the present invention results in more accurate than previously available estimates of partial pressure blood gas pressures and does so while eliminating a significant risk for injury to the patient.

31 Claims, 3 Drawing Sheets

U.S. PATENT DOCUMENTS

| | | |
|---|---|---|
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman et al. |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,938,218 A | 7/1990 | Goodman et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,285,784 A | 2/1994 | Seeker |
| 5,298,015 A | 3/1994 | Komatsuzaki et al. |
| 5,342,376 A | 8/1994 | Ruff |
| 5,344,415 A | 9/1994 | Debusk et al. |
| 5,358,494 A | 10/1994 | Svedman |
| 5,437,622 A | 8/1995 | Carion |
| 5,437,651 A | 8/1995 | Todd et al. |
| 5,474,065 A | 12/1995 | Meathrel et al. |
| 5,497,771 A | 3/1996 | Rosenheimer |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,827,181 A | 10/1998 | Dias et al. |
| 5,879,292 A * | 3/1999 | Sternberg et al. .......... 600/300 |
| 6,071,267 A | 6/2000 | Zamierowski |
| 6,113,541 A | 9/2000 | Dias et al. |
| 6,135,116 A | 10/2000 | Vogel et al. |
| 6,142,982 A | 11/2000 | Hunt et al. |
| 6,206,835 B1 | 3/2001 | Spillman, Jr. et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,856,821 B2 | 2/2005 | Johnson |
| 2002/0077661 A1 | 6/2002 | Saadat |
| 2002/0115951 A1 | 8/2002 | Norstream et al. |
| 2002/0120185 A1 | 8/2002 | Johnson |
| 2002/0143286 A1 * | 10/2002 | Tumey ...................... 604/11 |

FOREIGN PATENT DOCUMENTS

| | | |
|---|---|---|
| AU | 745271 | 3/2002 |
| AU | 755496 | 12/2002 |
| CA | 2005436 | 6/1990 |
| DE | 26 40 413 A1 | 3/1978 |
| DE | 43 09 478 A1 | 9/1994 |
| DE | 295 04 378 U1 | 9/1995 |
| EP | 0117632 A2 | 1/1984 |
| EP | 0100148 | 2/1984 |
| EP | 0161865 | 11/1985 |
| EP | 0358 302 | 3/1990 |
| EP | 1 018 967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2333965 A | 8/1999 |
| GB | 2329127 B | 8/2000 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO/94/20041 | 9/1994 |
| WO | WO 96/05873 | 2/1996 |
| WO | WO 97/18007 | 5/1997 |

| | | |
|---|---|---|
| WO | WO 99/13793 | 9/1998 |

OTHER PUBLICATIONS

Susan Mendez-Eastman, RN; When Wounds Won't Heal, RN Jan. 1998, vol. 61(1); Medical Economics Company, Inc., Montvale, NJ, USA.

James H. Blackburn, II, MD. et al; Negative-Pressure Dressings as a Bolster for Skin Grafts; Annals of Plastic Surgery, vol. 40, No. 5, May 1998, pp. 453-457; . . . .

John Masters; Letter to the editor; British Journal of Plastic Surgery, 1998, vol. 51(3), p. 267; Elsevier Science/The British Association of Plastic Surgeons, UK.

S.E. Greer, et al; The Use of Subatmospheric Pressure Dressing Therapy to Clos Lymphocutaneous Fistulas of the Groin; British Journal of Plastic Surgery (2000), 53 . . . .

George V. Letsou, M.D., et al; Stimulation of Adenylate Cyclase Activity in Cultured Endothelial Cells Subjected to Cyclic Stretch; Journal of Cardiovascular Surgery, 31, 1990.

PCT International Search Report; PCT international application PCT/GB98/02713; Jun. 8, 1999.

PCT Written Opinion; PCT international application PCT/GB98/02713; Jun. 8, 1999.

PCT International Examination and Search Report, PCT international application PCT/GB96/02802; Jan. 15, 1998 and Apr. 29, 1997.

PCT Written Opinion, PCT international application PCT/GB/96/02802; Sep. 3, 1997.

Kostyuchenok, B.M, et al. ;Vacuum Treatment in the Surgical Management of Purulent Wounds; Vestnik Khirurgi, Sep. 1986.

Davydov, Yu. A., et al; Vacuum Therapy in the Treatment of Purulent Lactation Mastitis; Vestnik Khirurgi, Sep. 1986.

Yusupov, Yu. N., et al; Active Wound Drainage, Vestnik Khirurgi, vol. 138, Issue 4, 1987.

Davydov, Yu. A., et al; Bacteriological and Cytological Assessment of Vacuum Therapy of Purulent Wounds; Vestnik Khirurgi, Oct. 1988.

Davydov, Yu. A., et al; Concepts For the Clinical-Biological Management of the Wound Process in the Treatment of Purulent Wounds by Means Vacuum Therapy; Vestnik Khirurgi.

Internation Search Report for PCT international application PCT/GB95/01983; Nov. 23, 1995.

Patent Abstract of Japan; JP4129536; Terumo Corporation; Apr. 30, 1992.

Orringer, Jay, et al., "Management of Wounds in Patients with Complex Enterocutaneous Fistulas", Surgery, Gynecology & Obstetrics, Jul. 1987, V. 165, pp. 79-80.

PCT International Search Report for PCT International Application PCT/GB98/02713; Jun. 8, 1999.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," *Current Problems in Modern Clinical Surgery: Interdepartmental Collection*, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," *Timok Medical Journal* 11 (1986), pp. 161-164 (copy and certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

* cited by examiner

SYSTEM FOR COMBINED TRANSCUTANEOUS BLOOD GAS MONITORING AND NEGATIVE PRESSURE WOUND TREATMENT

RELATED APPLICATIONS

This application is a continuation of U.S. patent application Ser. No. 10/085,321 filed Feb. 28, 2002 now U.S. Pat. No.6,856,821, which is a continuation-in-part, of U.S. patent application Ser. No. 09/579,755, entitled "Transcutaneous Blood Gas Monitoring with Vacuum Pefusion," filed on May 26, 2000, now abandoned which claims priority from Provisional Application No. 60/136293, filed May 27, 1999.

FIELD OF THE INVENTION

The present invention relates to the monitoring of blood gases during vacuum assisted wound healing. More particularly, the invention relates to a method and system for the transcutaneous monitoring of blood gases wherein said monitoring is enhanced by application of a vacuum pressure in the region of skin under evaluation, and during which negative pressure therapy is being applied to an adjacent or proximal wound site.

BACKGROUND OF THE INVENTION

Transcutaneous blood gas monitoring is known in the relevant arts as a method by which measurements of skin-surface gas pressures may be utilized to estimate arterial partial pressures of the gas of interest. In particular, skin surface oxygen or carbon dioxide pressure $PO_2$ or $PCO_2$, respectively, is measured by a locally applied, electrochemically based device in order to develop an estimate of arterial partial pressure of oxygen or carbon dioxide $P_aO_2$ or $P_aCO_2$, respectively. The obtained estimate is then made available to the clinician as an aid for the routine or emergency assessment of any of a variety of known cardiopulmonary functions.

In practice, a condition of hyperperfusion is indicated in the region of skin adjacent the applied device in order to enhance the flow of arterial blood gases toward and through the skin surface. To date, this hyperperfusion condition has been established by local heating of the skin with an electrode in order to distend the arterial capillaries. Unfortunately, such local heating carries with it an increased risk for tissue injury—erythema, blisters, burns and skin tears being among the documented complications. In addition, some debate exists within the art as to whether the increased local metabolic rate concomitant the application of heat counteracts the intended perfusion effect. If so, false readings may result, which may ultimately lead to inappropriate treatment of the patient.

The use of transcutaneous blood gas monitoring can be particularly advantageous when used in conjunction with negative pressure therapy for vacuum induced healing of open wounds or other tissue damage. Vacuum induced healing of open wounds has recently been popularized by Kinetic Concepts, Inc. of San Antonio, Texas. by its commercially available V.A.C.® product line. The vacuum induced healing process has been described in commonly assigned U.S. Pat. No. 4,969,880 issued on Nov. 13, 1990 to Zamierowski, as well as its continuations and continuations in part, U.S. Pat. No. 5,100,396, issued on Mar. 31, 1992, U.S. Pat. No. 5,261, 893, issued Nov. 16,1993, and U.S. Pat. No. 5,527,293, issued Jun. 18, 1996, the disclosures of which are incorporated herein by this reference. Further improvements and modifications of the vacuum induced healing process are also described in U.S. Pat. No. 6071,267, issued on Jun. 6, 2000 to Zamieroweki and U.S. Pat. Nos. 5,636,643 and 5,645,081 issued to Argenta et al. on Jun. 10,1997 and Jul. 8, 1997 respectively, the disclosures of which are incorporated by reference as though fully set forth herein. Additional improvements have also been described in U.S. Pat. No. 6,142,982, issued on Nov. 7. 2000 to Hunt et al.

The use of transcutaneous blood gas monitoring in conjunction with V.A.C.® therapy allows for monitoring of blood gases within and around the wound bed. Blood gases can be an indicative factor of wound healing progression. Crucial information can be ascertained as to the progression of the wound without disturbing the wound dressing.

It is therefore a primary object of the present invention to improve over the prior art by providing a method and apparatus for the transcutaneous monitoring of blood gases wherein local heating for hyperperfusion is eliminated, thereby eliminating a significant patient hazard and wherein the concomitant metabolic effects of local heating are likewise eliminated, thereby reducing the likelihood for misdiagnosis leading to inappropriate treatment regimen.

Hyperperfusion through local heating also requires a prolonged warm up and stabilization time following electrode placement in order for equilibration and calibration of the electrochemical transducer. As a result, operator time is generally wasted in the administration of a transcutaneous blood gas evaluation. Additionally, transcutaneous blood gas monitors are either not available for emergency use or must be made available with an operated in a standby mode. Such a standby mode requires additional hardware and generally shortens the electrode lifecycle.

It is therefore a further object of the present invention to improve over the prior art by providing a method and apparatus for the transcutaneous monitoring of blood gases wherein the apparatus is available for full operation on short notice without requirement for additional and/or lifecycle shortening hardware.

It is still a further object of the present invention to provide a system and method that combines the advantages of a non-invasive blood gas monitoring device with the effectiveness of negative pressure therapy upon wounds, so as to further improve the efficacy of negative pressure therapy on the treatment of wounds and other tissue treatments.

Finally it is still a further object of the present invention to improve over the prior art by providing a method and apparatus for the transcutaneous monitoring of blood gases wherein the above-described objects are implemented without sacrifice to patient safety or device efficacy, but wherein unnecessary hardware and software is nonetheless avoided, thereby conserving the ever more limited healthcare dollar.

SUMMARY OF THE INVENTION

In accordance with the foregoing objects, the present invention—a method and system for the transcutaneous monitoring of blood gases and vacuum assisted wound closure-generally comprises a blood gas data acquisition device, a vacuum source and a blood gas transducer unit. The blood gas transducer is adapted for application to a patient's skin and administration of a local vacuum at the area of patient application. It further comprises an electrochemical blood gas transducer, well known to those of ordinary skill in the art, which is disposed entirely within the local vacuum at the area of patient application. The transducer may also be disposed within a wound site, or an area immediately adjacent a wound site that is being treated by negative pressure therapy. The use of negative pressure therapy may include a porous, semi-rigid screen placed within a wound bed, a cover for maintaining a negative pressure within the wound bed that is placed over the screen and wound bed, and a vacuum source in fluid communication with the screen. Additionally, a canister may be disposed between the screen and vacuum source, for the collection of fluids that may emanate from the wound during application of negative pressure by the vacuum source. A flexible tube or similar device is used to communicate between the screen and vacuum source.

It is contemplated that the transducer may be incorporated within the screen, or alternatively placed as a separate element below the screen to be in direct contact with the wound bed, within a depression or cut-out of the screen, above the screen, or separate from the screen but immediately adjacent the wound bed.

The blood gas transducer unit is in fluid communication with the vacuum source through an interposed vacuum hose and in electrical communication with the blood gas data acquisition device through an interposed electrical cable. The vacuum source, which comprises a vacuum pump operated by a pump motor is placed in fluid communication with the blood gas transducer unit in order to induce a condition of hyperperfusion in the locality of the electrochemical blood has transducer. Under the control of the microcontroller, or equivalent means, the blood gas data acquisition device is then utilized to capture this measure to arrive at an estimate of arterial partial pressure of oxygen or carbon dioxide, accordingly. Because vacuum induced perfusion produces the requisite condition of hyperperfusion without local heating and, therefore, without acceleration of the local metabolic function, the present invention results in more accurate than previously available estimates of partial blood gas pressures and does so while eliminating a significant risk for injury to the patient.

The same vacuum source, or alternatively a second vacuum source, may be utilized to provide negative pressure at the wound site by communicating with the screen placed within the wound site, by means of a tube or similar device.

Because the application of vacuum perfusion to the patient presents at least some risk for contamination of the vacuum source and blood gas data acquisition device, the preferred embodiment of the present invention further comprises a transducer interface module particularly adapted for the reduction or elimination of contamination risk. According to the invention, the transducer interface module comprises a male and female interface pair, wherein the male portion is adapted into the female portion and thereby establishes communication between the blood gas transducer unit and the vacuum source and blood gas data acquisition device.

In implementing the male plug, a hydrophobic membrane filter—known to those of ordinary skill in the art—is interposed in the vacuum hose, thereby eliminating the opportunity for contaminants to pass from the patient to the vacuum source or blood gas data acquisition device. While the preferred embodiment of the present invention comprises a throw-away male plug, vacuum hose, electrical cable and blood gas transducer unit, those of ordinary skill in the art will recognize that each of these components can be made reusable with implementation of proper, known sterilization techniques. In this latter case, the hydrophobic membrane filter is preferably replaceable.

Finally, many other features, objects and advantages of the present invention will be apparent to those of ordinary skill in the relevant arts, especially in light of the foregoing discussions and the following drawings and exemplary detailed description.

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims that may be drawn hereto.

Figure 1:
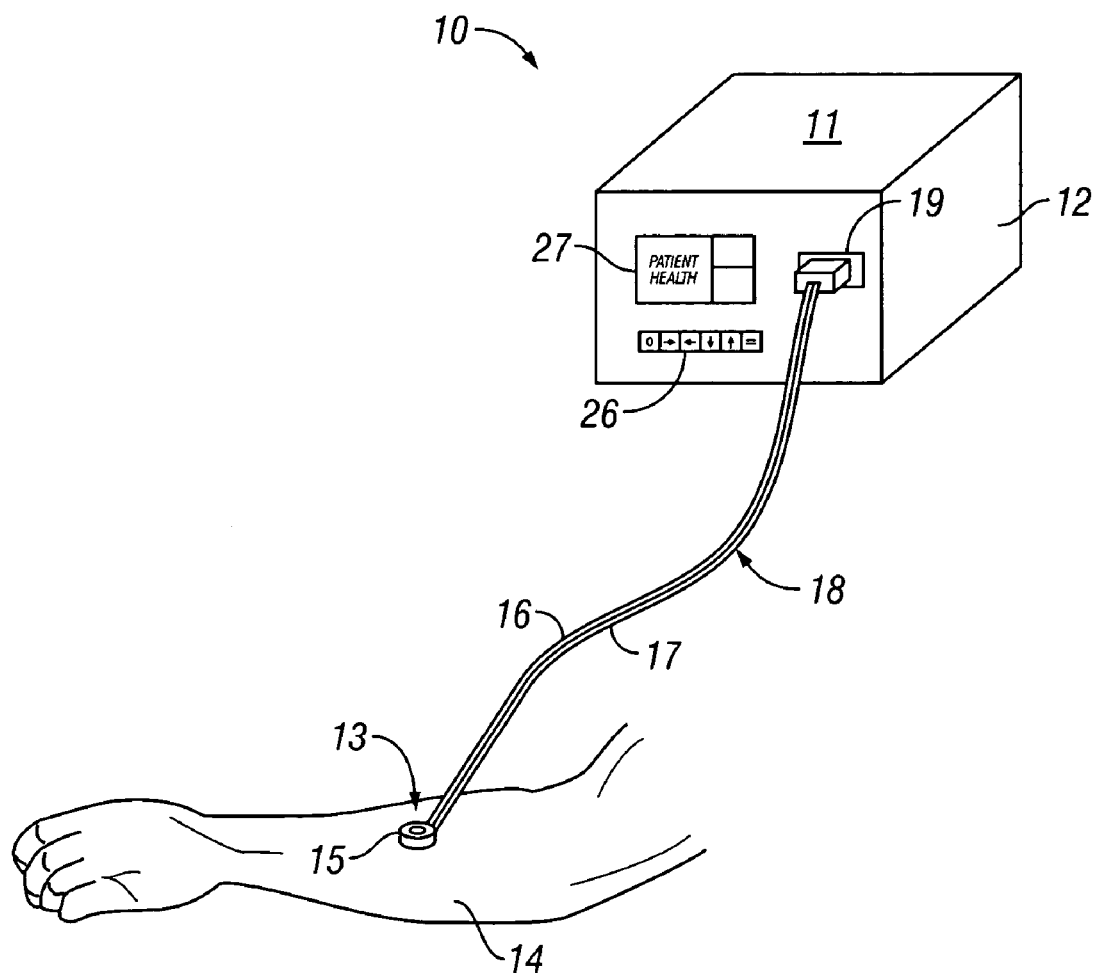
FIG. 1 shows, in perspective view, the preferred embodiment of the transcutaneous blood gas monitoring apparatus of the present invention, as employed with a human subject.

Referring now to FIG. 1, the preferred embodiment of the transcutaneous blood gas monitoring system 10 of the present invention is shown to generally comprise a blood gas data acquisition device 11, a vacuum source 12 and a blood gas transducer unit 13. As shown in FIG. 1, the blood gas transducer unit 13 is adapted for application to a patient's skin 14. In alternative embodiments, not shown, the blood gas transducer may be applied within a wound bed 30 or disposed within a screen 32 placed within the wound bed 30. As will be better understood further herein, the blood gas transducer unit 13 is also adapted for administration of a local vacuum at the area of the patient application. Finally, the blood gas transducer unit 13 comprises an electrochemical blood gas transducer 15, well known to those of ordinary skill in the art, which is disposed entirely within the local vacuum at the area of patient application.

As also depicted in FIG. 1, the blood gas transducer unit 13 is in fluid communication with the vacuum source 12 through an interposed vacuum hose 16 and in electrical communication with the blood gas data acquisition device 11 through an interposed electrical cable 17. Although those of ordinary skill in the art will recognize many substantial equivalents, the preferred embodiment of the present invention comprises a unitary hose and cable pair 18. Such a unitary pair 18 serves to reduce clutter in the patient care environment, thereby reducing the likelihood of either the hose 16 or cable 17 becoming entangled with other tubes, cables or equipment. Further, and as will be better understood further herein, such a unitary pair 18 is especially adapted for use with the preferred embodiment of the novel transducer interface module 19 of the present invention.

Figure 2:
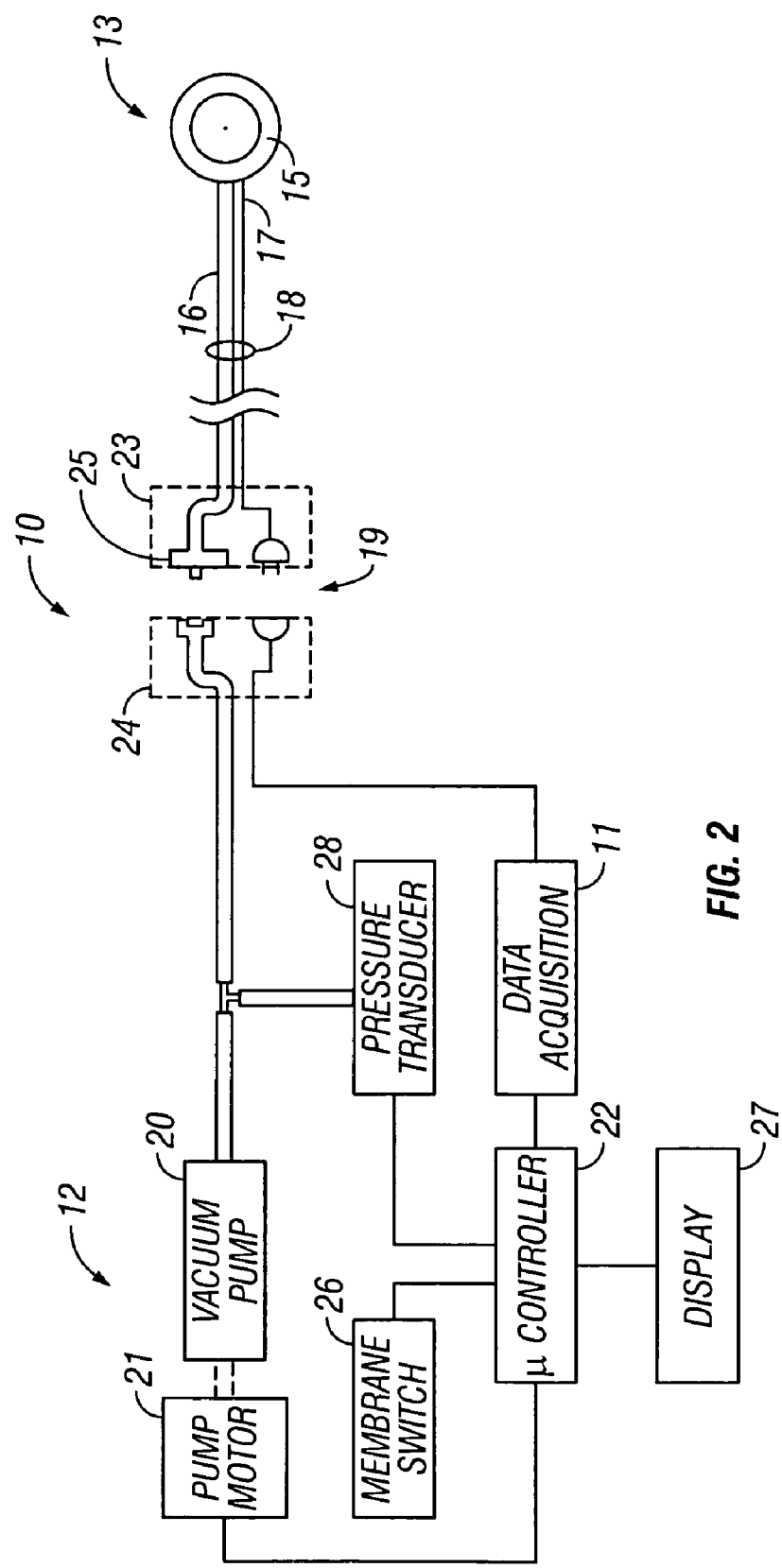
FIG. 2 shows, in schematic block diagram, details of the apparatus of FIG. 1.

According to the preferred embodiment of the present invention, in FIG. 2, the vacuum source 12 comprises a vacuum pump 20 operated by a pump motor 21. Those of ordinary skill in the art, however, will recognize many substantially equivalent embodiments for the vacuum source 12 including, for example, a central hospital vacuum or suction source or an integral pump and motor. In any case, all such equivalents are considered within the scope of the invention, which requires only a vacuum source 12 of the character otherwise described herein and which is capable of providing suction in the range of about 50 mmHg through 250 mmHg.

In operation, the vacuum source 12 is placed in fluid communication with the blood gas transducer unit 13 in order to induce a condition of hyperperfusion in the locality of the electrochemical blood gas transducer 15. Under the control of a microcontroller 22, or equivalent means, the blood gas data acquisition device 11 is then utilized to capture a measure of skin surface oxygen and/or carbon dioxide pressure. The microcontroller 22 can then utilize this measure to arrive at an estimate of arterial partial pressure of oxygen or carbon dioxide, accordingly. Because vacuum induced perfusion produces the requisite condition of hyperperfusion without local heating and, therefore, without acceleration of the local metabolic function, the present invention results in more accurate than previously available estimates of partial blood gas pressures and does so while eliminating a significant risk for injury to the patient.

Because the application of vacuum to the patient presents at least some risk for contamination of the vacuum source 12 and blood gas data acquisition device 11, the preferred embodiment of the present invention further comprises a transducer interface module 19 particularly adapted for the reduction or elimination of contamination risk. According to the invention, the transducer interface module 19 comprises a male 23 and female 24 interface pair, wherein the male portion 23 is adapted to plug into the female portion 24 and thereby establish communication between the blood gas transducer unit 13 and the vacuum source 12 and blood gas acquisition device 11.

In implementing the male plug 23, a hydrophobic membrane filter 25—known to those of ordinary skill in the art—is interposed in the vacuum hose 16, thereby eliminating the opportunity for contaminants to pass from the patient 14 to the vacuum source 12 or blood gas data acquisition device 11. While the preferred embodiment of the present invention comprises a throw-away male plug 23, vacuum hose 16, electrical cable 17 and blood gas transducer unit 13, those of ordinary skill in the art will recognize that each of these components can be made reusable with implementation of proper, known sterilization techniques. In this latter case, the hydrophobic membrane filter 25 is preferably replaceable.

Figure 3:
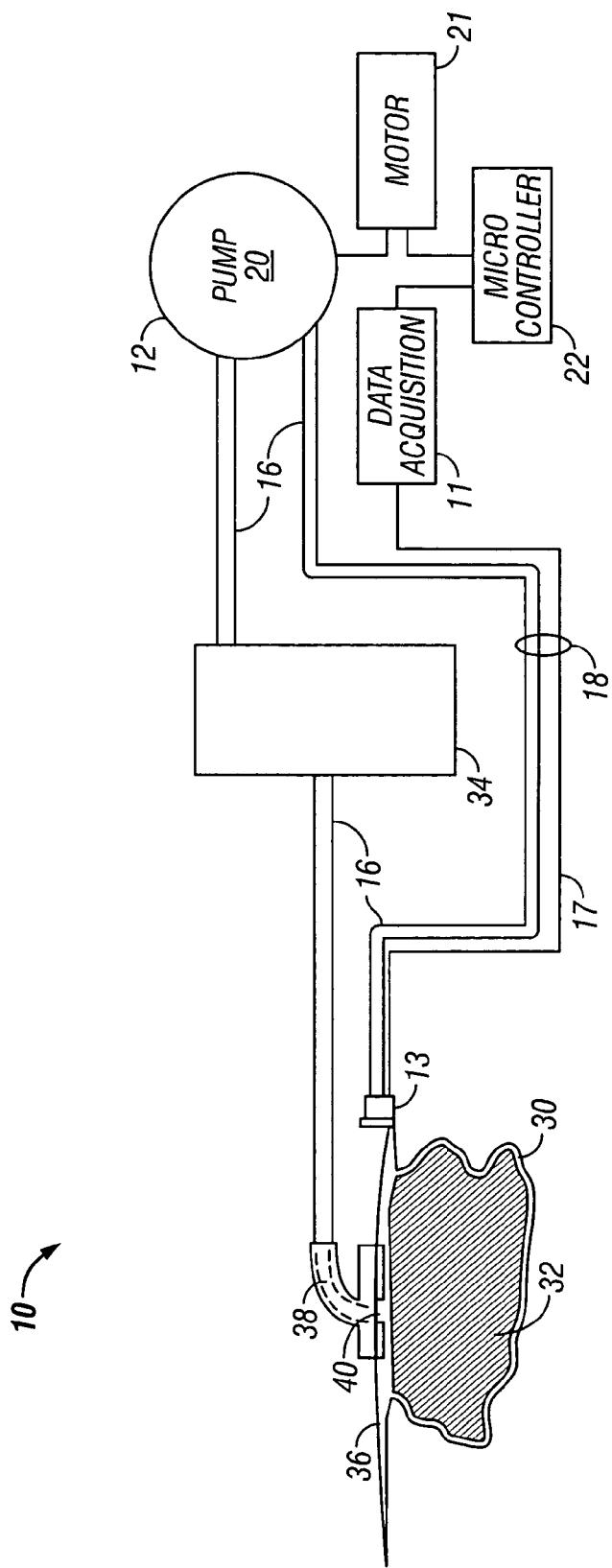
FIG. 3 shows, in schematic block diagram, a transcutaneous blood gas monitoring device utilized in conjunction with a negative pressure therapy device.

Referring now to FIG. 3, a collection canister 34 may be interposed between the vacuum source 12 and the screen 32. As suction is applied, fluids may be drawn from the wound 30 and collected in the canister 34. A common vacuum source 12 may be utilized to provide vacuum perfusion to the blood gas transducer 13 and negative pressure to the wound site 30. A seal 36 is adhered over the screen 32 in order to maintain negative pressure within the wound site 30. The seal 36 may be comprised of an elastomeric material. The screen 32 is preferably comprised of poly-vinyl alcohol foam, or alternatively a polyurethane porous sheet. It is to be understood that any semi-rigid and porous material may be utilized as a screen 32 within the wound bed 30. The tube 16 may be in direct fluid communication with the screen 32 (not shown), or connected to an adapter 38 that is adhered over an opening 40 in the seal 36. It is preferable that the tube 16 is bifurcated at a position between the vacuum source 12 and the canister 34 so that fluids being drawn from the wound site 30 do not interfere with the vacuum perfusion of the blood gas transducer 13.

In an alternate embodiment, not shown, a separate vacuum source may be utilized to provide negative pressure to the wound site 30 and another vacuum source utilized to provide vacuum perfusion to the blood gas transducer 13.

While the foregoing description is exemplary of the preferred embodiment of the present invention, those of ordinary skill in the relevant arts will recognize the many variations, alterations, modifications, substitutions and the like as are readily possible, especially in light of this description and the accompanying drawings. For example, in FIG. 1, a membrane or other like switch pad 26 may be implemented for user control of the transcutaneous blood gas monitor 10 and/or a display, printer or other output device 27 may be provided for monitoring and/or recording of estimated partial pressures. Likewise, in FIG. 2. a pressure transducer 28 may be, and preferably is, provided for monitoring and control of the vacuum applied to the patient's skin 14. In any case, because the scope of the present invention is much broader than any particular embodiment, the foregoing detailed description should not be construed as a limitation of the scope of the present invention, which is limited only by the claims that may be drawn hereto. What is claimed is:

What is claimed is:

1. A transcutaneous blood gas monitoring device particularly suited for application to a site on a patient's skin under a local vacuum, comprising:
   a non-invasive blood gas data acquisition device, the non-invasive blood gas data acquisition device adapted to measure skin surface oxygen and carbon dioxide pressure;
   a vacuum source in fluid communication with a wound site in proximity to the site on the patient's skin for applying a negative pressure to the wound site;
   an electrochemical blood gas transducer unit in fluid communication with said vacuum source;
   a transducer interface module communicating between the electrochemical blood gas transducer unit, the vacuum source and the non-invasive blood gas data acquisition device and adapted to reduce or eliminate contamination; and
   a screen formed to fit within said wound site.

2. The transcutaneous blood gas monitoring device of claim 1, wherein the vacuum source is in fluid communication with the electrochemical blood gas transducer unit through an interposed vacuum hose.

3. The transcutaneous blood gas monitoring device of claim 2, wherein the electrochemical blood gas transducer unit is in electrical communication with the non-invasive blood gas data acquisition device through an interposed electrical cable.

4. The transcutaneous blood gas monitoring device of claim 3, wherein the interposed vacuum hose and the interposed electrical cable comprise a unitary hose and cable pair for reduction of entanglement with other tubes, cables or equipment.

5. The transcutaneous blood gas monitoring device of claim 4, further comprising a hydrophobic membrane filter interposed in the interposed vacuum hose.

6. The transcutaneous blood gas monitoring device of claim 5, wherein the hydrophobic membrane filter is disposable.

7. The transcutaneous blood gas monitoring device of claim 3, wherein the non-invasive blood gas data acquisition device monitors healing of the wound site.

8. The transcutaneous blood gas monitoring device of claim 3, further comprising:
   a seal for maintaining the negative pressure within said wound site during application of negative pressure.

9. The transcutaneous blood gas monitoring device of claim 3, further comprising a collection canister interposed between the vacuum source and the screen.

10. The transcutaneous blood gas monitoring device of claim 9, wherein the interposed vacuum hose is bifurcated at a position between the vacuum source and the collection canister to prevent fluids drawn from the wound site from interfering with the electrochemical blood gas transducer unit.

11. The transcutaneous blood gas monitoring device of claim 3, further comprising a controller for governing actions of said non-invasive blood gas data acquisition device.

12. The transcutaneous blood gas monitoring device of claim 1, wherein the transducer interface module comprises a male and female interface pair, wherein the male interface is adapted to plug into the female interface and establish communication between the electrochemical blood gas transducer unit, the vacuum source and the non-invasive blood gas acquisition device.

13. The transcutaneous blood gas monitoring device of claim 1, wherein the vacuum source comprises a vacuum pump operated by a pump motor.

14. The transcutaneous blood gas monitoring device of claim 1, wherein the electrochemical blood gas transducer unit is incorporated within the screen.

15. The transcutaneous blood gas monitoring device of claim 1, wherein the screen is in fluid communication with the vacuum source.

16. The transcutaneous blood gas monitoring device of claim 1, further comprising a second vacuum source adapted to provide negative pressure at the wound site by communicating with the screen.

17. The transcutaneous blood gas monitoring device of claim 1, wherein the vacuum source is capable of providing suction in a range of about 50 mmHg to about 250 mmHg.

18. A transcutaneous blood gas monitoring device particularly suited for application to a site on a patient's skin under a local vacuum, comprising:
  a non-invasive blood gas data acquisition device;
  a vacuum source in fluid communication with a wound site in proximity to the site on the patient's skin for applying a negative pressure to the wound site;
  an electrochemical blood gas transducer unit in fluid communication with said vacuum source, the electrochemical blood gas transducer unit in electrical communication with the non-invasive blood gas data acquisition device through an interposed electrical cable, and the vacuum source in fluid communication with the electrochemical blood gas transducer unit through an interposed vacuum hose;
  a transducer interface module communicating between the electrochemical blood gas transducer unit, the vacuum source and the non-invasive blood gas data acquisition device and adapted to reduce or eliminate contamination;
  a screen formed to fit within said wound site; and
  a collection canister interposed between the vacuum source and the screen, wherein the interposed vacuum hose is bifurcated at a position between the vacuum source and the collection canister to prevent fluids drawn from the wound site from interfering with the electrochemical blood gas transducer unit.

19. The transcutaneous blood gas monitoring device of claim 18, wherein the interposed vacuum hose and the interposed electrical cable comprise a unitary hose and cable pair for reduction of entanglement with other tubes, cables or equipment.

20. The transcutaneous blood gas monitoring device of claim 19, further comprising a hydrophobic membrane filter interposed in the interposed vacuum hose.

21. The transcutaneous blood gas monitoring device of claim 20, wherein the hydrophobic membrane filter is disposable.

22. The transcutaneous blood gas monitoring device of claim 18, wherein the non-invasive blood gas data acquisition device monitors healing of the wound site.

23. The transcutaneous blood gas monitoring device of claim 18, further comprising:
  a seal for maintaining the negative pressure within said wound site during application of negative pressure.

24. The transcutaneous blood gas monitoring device of claim 18, further comprising a controller for governing actions of said non-invasive blood gas data acquisition device.

25. The transcutaneous blood gas monitoring device of claim 18, wherein the transducer interface module comprises a male and female interface pair, wherein the male interface is adapted to plug into the female interface and establish communication between the electrochemical blood gas transducer unit, the vacuum source and the non-invasive blood gas acquisition device.

26. The transcutaneous blood gas monitoring device of claim 18, wherein the vacuum source comprises a vacuum pump operated by a pump motor.

27. The transcutaneous blood gas monitoring device of claim 18, wherein the electrochemical blood gas transducer unit is incorporated within the screen.

28. The transcutaneous blood gas monitoring device of claim 18, wherein the screen is in fluid communication with the vacuum source.

29. The transcutaneous blood gas monitoring device of claim 18, further comprising a second vacuum source adapted to provide negative pressure at the wound site by communicating with the screen.

30. The transcutaneous blood gas monitoring device of claim 18, wherein the non-invasive blood gas data acquisition device is adapted to measure skin surface oxygen and carbon dioxide pressure.

31. The transcutaneous blood gas monitoring device of claim 18, wherein the vacuum source is capable of providing suction in a range of about 50 mmHg to about 250 mmHg.

* * * * *